(12) United States Patent
Howard et al.

(10) Patent No.: US 12,023,084 B2
(45) Date of Patent: *Jul. 2, 2024

(54) PROFILE PARAMETER SELECTION ALGORITHM FOR ELECTROPORATION

(71) Applicant: Medtronic, Inc., Minneapolis, MN (US)

(72) Inventors: Brian T. Howard, Minneapolis, MN (US); Steven J. Fraasch, Maple Grove, MN (US); Mark T. Stewart, Lino Lakes, MN (US); John Vandanacker, Rockford, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/577,775

(22) Filed: Jan. 18, 2022

(65) Prior Publication Data
US 2022/0133389 A1     May 5, 2022

Related U.S. Application Data

(62) Division of application No. 15/427,534, filed on Feb. 8, 2017, now Pat. No. 11,229,478.

(51) Int. Cl.
*A61B 18/12* (2006.01)
*A61B 18/14* (2006.01)
(Continued)

(52) U.S. Cl.
CPC .......... *A61B 18/1206* (2013.01); *A61B 18/14* (2013.01); *A61N 1/327* (2013.01);
(Continued)

(58) Field of Classification Search
CPC . A61B 18/1206; A61B 18/14; A61B 18/1492; A61B 2018/00357;
(Continued)

(56) References Cited

U.S. PATENT DOCUMENTS

| 2010/0023004 A1 | 1/2010 | Francischelli et al. |
| 2013/0218157 A1 | 8/2013 | Callas et al. |

(Continued)

FOREIGN PATENT DOCUMENTS

| CN | 103093081 A | 5/2013 |
| CN | 105283143 A | 1/2016 |
| WO | 2017024123 A1 | 2/2017 |

OTHER PUBLICATIONS

China National Intellectual Property Administration First Office Action for Application No. 201880010687.3 dated Mar. 14, 2022 (13 pages including English translation).

(Continued)

*Primary Examiner* — Khadijeh A Vahdat
(74) *Attorney, Agent, or Firm* — Michael Best & Friedrich LLP (57) ABSTRACT

A method of determining a pulsed field ablation waveform parameter for creating a desired lesion characteristic in cardiac tissue. The method of provides an electrosurgical generator configured to deliver electroporation pulses, the generator configured to: load predetermined waveform parameters ($y_i$); load predetermined modeling data ($x_i$); accept entry of a user inputted desired lesion characteristic ($u_i$); and determine at least one corresponding pulsed field ablation waveform parameter based on ($u_i$), ($y_i$); and ($x_i$).

24 Claims, 4 Drawing Sheets

(51) Int. Cl.
*A61N 1/32* (2006.01)
*G06F 30/20* (2020.01)
*A61B 18/00* (2006.01)

(52) U.S. Cl.
CPC .... *G06F 30/20* (2020.01); *A61B 2018/00357* (2013.01); *A61B 2018/00613* (2013.01); *A61B 2018/0075* (2013.01); *A61B 2018/00761* (2013.01); *A61B 2018/00767* (2013.01); *A61B 2018/00779* (2013.01); *A61B 2018/00791* (2013.01); *A61B 2018/00827* (2013.01); *A61B 2018/00839* (2013.01); *A61B 2018/00875* (2013.01); *A61B 2018/00892* (2013.01); *A61B 2018/1253* (2013.01); *A61B 2018/126* (2013.01); *A61B 2018/1407* (2013.01); *A61B 2018/1467* (2013.01); *A61B 18/1492* (2013.01)

(58) Field of Classification Search
CPC .. A61B 2018/00613; A61B 2018/0075; A61B 2018/00761; A61B 2018/00767; A61B 2018/00779; A61B 2018/00791; A61B 2018/00827; A61B 2018/00839; A61B 2018/00875; A61B 2018/00892; A61B 2018/1253; A61B 2018/126; A61B 2018/1407; A61B 2018/1467
See application file for complete search history.

(56) References Cited

U.S. PATENT DOCUMENTS

2014/0180273 A1 6/2014 Nair
2015/0088120 A1 3/2015 Garcia et al.

OTHER PUBLICATIONS

International Search Report and Written Opinion dated Apr. 9, 2018, for corresponding International Application No. PCT/US2018/015863; International Filing Date: Jan. 30, 2018 consisting of 4-pages.
Pucihar G et al: Equivalent Pulse Parameters for Electroporation IEEE transactions on biomedical Engineering, IEEE Service Centre, Piscataway, NJ, USA, vol. 58, No. 11, Nov. 11, 2011 (Nov. 11, 2011), pp. 3279-3288, XP011408549, ISSN: 0018-9294, DOI: 10.1109/TBME. 2011.2167232 the whole document.

PROFILE PARAMETER SELECTION ALGORITHM FOR ELECTROPORATION

CROSS-REFERENCE TO RELATED APPLICATION

This application is a divisional of and claims the benefit of U.S. application Ser. No. 15/427,534, filed Feb. 8, 2017, now U.S. Pat. No. 11,229,478.

STATEMENT REGARDING FEDERALLY SPONSORED RESEARCH OR DEVELOPMENT n/a

TECHNICAL FIELD

This disclosure relates to a method and system for determining electroporation parameters based on desired lesion characteristics.

BACKGROUND

Electroporation is the application of an electric field to cells in order to increase the permeability of the cell membrane. Pulsed field ablation ("PFA") which can cause reversible or irreversible electroporation, is a non-thermal ablation technique that creates lesions in desired areas to treat conditions such as cardiac arrhythmias, and to ablate areas of tissues and/or organs in the body. For treating cardiac arrhythmias, for example, PFA can be performed to modify tissue, such as to stop aberrant electrical propagation and/or disrupt aberrant electrical conduction through cardiac tissue.

PFA includes application of short pulsed electric fields (PEF), which may reversibly or irreversibly destabilize cell membranes through electro-permeabilization, but generally do not affect the structural integrity of the tissue components, including the acellular cardiac extracellular matrix. The nature of PFA allows for very brief periods of therapeutic energy delivery, on the order of tens or hundreds of milliseconds in duration. Further, when targeting cardiomyocytes, PFA may not cause collateral damage to non-targeted tissue as frequently or as severely as thermal ablation techniques. Additionally, therapeutic agents may be preferentially introduced into the cells of targeted tissue that are exposed to PEF having reversible membrane permeabilization.

In PFA systems, the user programs, or otherwise manually enters, the desired parameters of the PEF delivered to the tissue into an electrosurgical generator configured to deliver electrical energy to the target tissue through an electrosurgical hand piece. That is, for a given delivery tool, target tissue, or environment, the user may select from waveform parameters such as the amplitude, size, shape, frequency, and repetition of the waveform. Upon entry of those parameters, the size of the lesion may be determined. In such an application, the size of the lesion (or affected area) such as the depth or breadth of the affected area is often the desired result. However, no system or method exists that allows the users to input into the electrosurgical generator the desired characteristics of a lesion for a particular tissue, such as length, width, and depth for use with PFA. For cardiac ablation energy delivery electrodes designed for placement on the endocardial surface or epicardial surface of the heart, achieving a desired depth or extent of lesion formation into the tissue is generally the objective. Alternative electrodes may be designed to ablate from within a confined space within the tissue, such as within the vasculature. In such placements, the electric field and resulting lesion extends radially outward from the electrode array, producing a lesion of a specific diameter surrounding the electrodes.

SUMMARY

The present application advantageously provides for a method of determining a pulsed field ablation waveform parameter for creating a desired lesion characteristic in cardiac tissue. The method of provides an electrosurgical generator configured to deliver electroporation pulses, the generator configured to: load predetermined waveform parameters ($y_i$); load predetermined modeling data ($x_i$); accept entry of a user inputted desired lesion characteristic ($u_i$); and determine at least one corresponding pulsed field ablation waveform parameter based on ($u_i$), ($y_i$); and ($x_i$).

In another aspect of this embodiment, the method includes coupling an electrosurgical device having a plurality of electrodes with the electrosurgical generator, the plurality of electrodes being configured to deliver electroporation pulses between an adjacent one of the plurality of electrodes.

In another aspect of this embodiment, wherein the predetermined modeling data ($x_i$) is a function of the predetermined waveforms parameters ($y_i$) and the user inputted desired lesion characteristic ($u_i$).

In another aspect of this embodiment, wherein the electrosurgical generator is configured to electrically couple with an electrosurgical medical device having a plurality of electrodes configured to deliver electroporation pulses between adjacent electrodes of the plurality of electrodes, and wherein the waveform parameters ($y_i$) include at least one from the group consisting of a number of pulses, a duration of each pulse, a number of pulse trains, an applied voltage, electrode polarity configuration, and inter-pulse timing.

In another aspect of this embodiment, wherein the user inputted desired lesion characteristic ($u_i$) includes at least one of the group consisting of lesion depth, lesion surface area, lesion width, and lesion length.

In another aspect of this embodiment, the method further includes delivering between 30-140 electroporation pulses to the cardiac tissue.

In another aspect of this embodiment, wherein a pulse width between each of the delivered electroporation pulse is between 3-6 µs.

In another aspect of this embodiment, wherein the electroporation pulses are delivered in at least 4 pulse trains.

In another aspect of this embodiment, wherein the determined at least one corresponding pulsed field ablation waveform parameter is at least one from the group consisting of an applied voltage amplitude and an applied electric field of the pulsed field ablation waveform.

In another aspect of this embodiment, wherein the method further includes determining whether the determined applied voltage amplitude is within a predetermined voltage threshold, and wherein the method further includes reducing the applied voltage amplitude when the determined applied voltage amplitude is above the predetermined voltage threshold.

In another aspect of this embodiment, wherein the user inputted desired lesion characteristic ($u_i$) is lesion depth, and wherein the method further includes setting accepting a user inputted range of lesion depth between 1 mm and 8 mm.

In another embodiment, an electrosurgical generator configured to deliver pulsed field ablation pulses to electroporate cardiac tissue includes a processor having processing circuitry configured to: load predetermined waveform parameters ($y_i$); load predetermined modeling data ($x_i$); accept entry of a user inputted desired lesion characteristic ($u_i$); and determine at least one corresponding pulsed field ablation waveform parameter based on ($u_i$), ($y_i$); and ($x_i$).

In another aspect of this embodiment, wherein the generator is further configured to electrically couple with an electrosurgical device having a plurality of electrodes, the plurality of electrodes being configured to deliver electroporation pulses between an adjacent one of the plurality of electrodes.

In another aspect of this embodiment, wherein the predetermined modeling data ($x_i$) is a function of the predetermined waveforms parameters ($y_i$) and the user inputted desired lesion characteristic ($u_i$).

In another aspect of this embodiment, wherein the electrosurgical generator is configured to electrically couple with an electrosurgical medical device having a plurality of electrodes configured to deliver electroporation pulses between adjacent electrodes of the plurality of electrodes, and wherein the waveform parameters ($y_i$) include at least one from the group consisting of a number of pulses, a duration of each pulse, a number of pulse trains, an applied voltage, electrode polarity configuration, and inter-pulse timing.

In another aspect of this embodiment, wherein the user inputted desired lesion characteristic ($u_i$) includes at least one of the group consisting of lesion depth, lesion surface area, lesion width, and lesion length.

In another aspect of this embodiment, wherein the determined at least one corresponding pulsed field ablation waveform parameter is at least one from the group consisting of an applied voltage amplitude and an applied electric field of the pulsed field ablation waveform.

In another aspect of this embodiment, the processing circuitry is further configured to determine whether the applied voltage amplitude is within a predetermined voltage threshold, and wherein the processing circuitry is further configured to reduce the applied voltage amplitude when the determined applied voltage amplitude is above the predetermined voltage threshold.

In another aspect of this embodiment, wherein the user inputted desired lesion characteristic ($u_i$) is lesion depth, and wherein the processing circuitry is configured to accept a user inputted range of lesion depth between 1 mm and 8 mm.

In yet another embodiment, an electrosurgical generator configured to deliver pulsed field ablation pulses to electroporate cardiac tissue includes a processor having processing circuitry configured to: load predetermined waveform parameters ($y_i$); load predetermined modeling data ($x_i$); accept entry of a user inputted desired lesion characteristic ($u_i$); determine an applied voltage amplitude based on ($u_i$), ($y_i$); and ($x_i$). The generator is configured to electrically couple with an electrosurgical device having a plurality of electrodes, the plurality of electrodes being configured to deliver electroporation pulses between an adjacent one of the plurality of electrodes, the plurality of electrodes being configured to define a substantially circumferential configuration. The processing circuitry is further configured to determine whether the applied voltage amplitude is within a predetermined voltage threshold, and wherein the processing circuitry is further configured to reduce the applied voltage amplitude when the determined applied voltage amplitude is above the predetermined voltage threshold.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein.

DETAILED DESCRIPTION

Before describing in detail exemplary embodiments, it is noted that the embodiments reside primarily in combinations of apparatus components and processing steps related to a PFA waveform profile parameter selection based on a desired lesion characteristic. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

Figure 1:
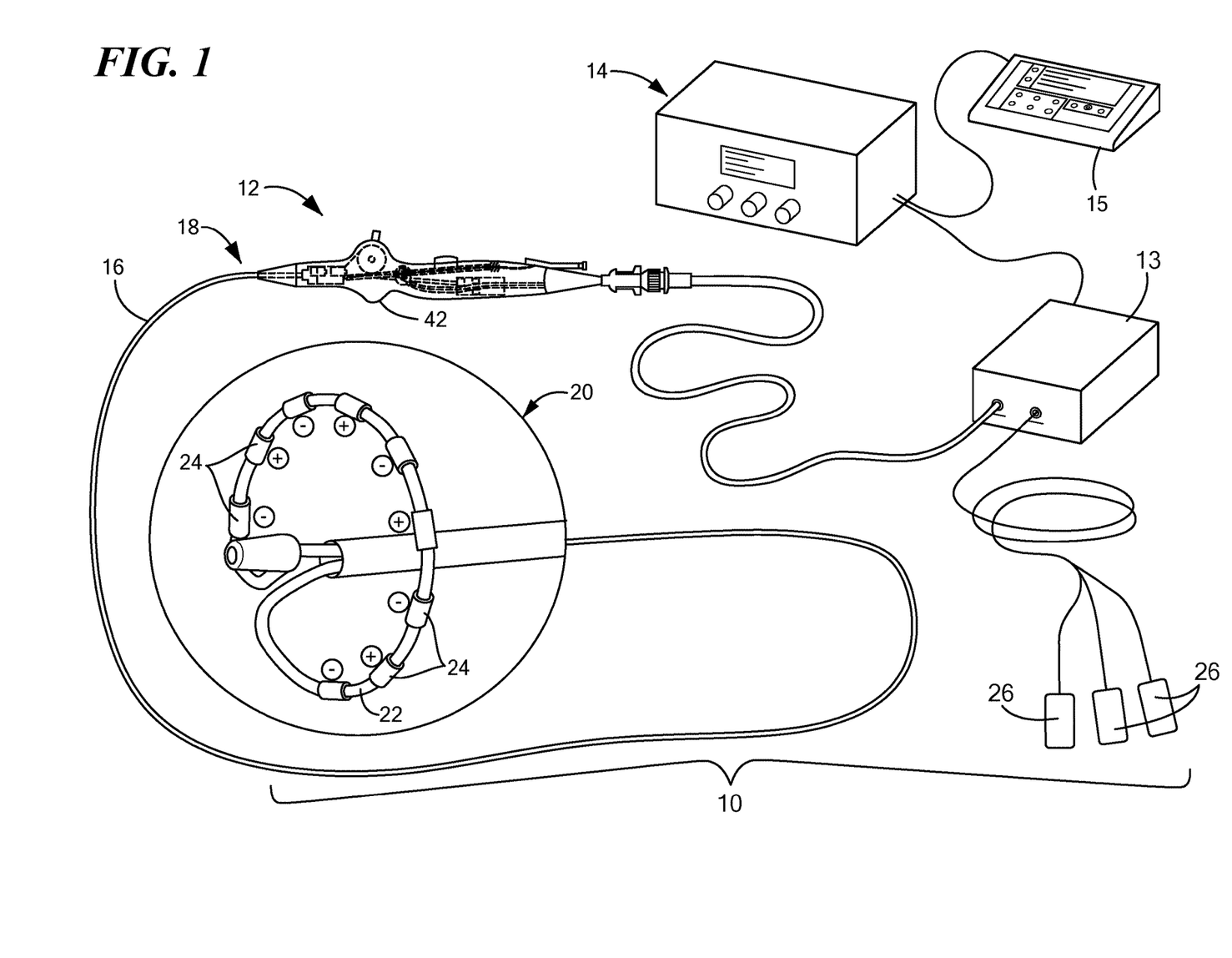
FIG. 1 is an exemplary electrosurgical generator with an associated handpiece and multi-electrode array for the delivery of PFA.

Referring now to the drawings where like reference designators refer to like elements there is shown in FIG. 1 an exemplary electrosurgical general configured to deliver electrical energy to irreversibly electroporate tissue and designated generally as "10." The system 10 generally includes a medical device 12 that may be coupled directly to an energy supply, for example, a pulsed field ablation generator 14 including an energy control, delivering and monitoring system or indirectly through a catheter electrode distribution system 13. A remote controller 15 may further be included in communication with the generator for operating and controlling the various functions of the generator 14. The medical device 12 may generally include one or more diagnostic or treatment regions for energetic, therapeutic and/or investigatory interaction between the medical device 12 and a treatment site. The treatment region(s) may deliver, for example, pulsed electroporation energy to a tissue area in proximity to the treatment region(s).

The medical device 12 may include an elongate body 16 passable through a patient's vasculature and/or positionable proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion of the elongate body 16 and the distal portion of the elongate body 16. The distal portion 20 may generally define the one or more treatment region(s) of the medical device 12 that are operable to monitor, diagnose, and/or treat a portion of a patient. The treatment region(s) may have a variety of configurations to facilitate such operation. In the case of purely bipolar pulsed field delivery, distal portion 20 includes electrodes that form the bipolar configuration for energy delivery where energy passes between one or more electrodes and one or more different electrodes on the same electrode array. In an alternate configuration, a plurality of the electrodes 24 may serve as one pole while a second device containing one or more electrodes (not pictured) would be placed to serve as the opposing pole of the bipolar configuration. For example, as shown in FIG. 1, the distal portion 20 may include an electrode carrier arm 22 that is transitionable between a linear configuration and an expanded configuration in which the carrier arm 22 has an arcuate or substantially circular configuration. The carrier arm 22 may include the plurality of electrodes 24 (for example, nine electrodes 24, as shown in FIG. 1) that are configured to deliver pulsed-field energy. Further, the carrier arm 22 when in the expanded configuration may lie in a plane that is substantially orthogonal to the longitudinal axis of the elongate body 16. The planar orientation of the expanded carrier arm 22 may facilitate ease of placement of the plurality of electrodes 24 in contact with the target tissue. Alternatively, the medical device 12 may be have a linear configuration with the plurality of electrodes 24. For example, the distal portion 20 may include six electrodes 24 linearly disposed along a common longitudinal axis.

The generator 14 may include processing circuitry including a first processor 17 in communication with one or more controllers and/or memories containing software modules containing instructions or algorithms to provide for the automated operation and performance of the features, sequences, calculations, or procedures described herein. The system 10 may further include three or more surface ECG electrodes 26 on the patient in communication with the generator 14 through the catheter electrode distribution system 13 to monitor the patient's cardiac activity for use in determining pulse train delivery timing at the desired portion of the cardiac cycle, for example, during the ventricular refractory period. In addition to monitoring, recording or otherwise conveying measurements or conditions within the medical device 12 or the ambient environment at the distal portion of the medical device 12, additional measurements may be made through connections to the multi-electrode catheter including for example temperature, electrode-tissue interface impedance, delivered charge, current, power, voltage, work, or the like in the generator 14 and/or the medical device 12. The surface ECG electrodes 26 may be in communication with the generator 14 for initiating or triggering one or more alerts or therapeutic deliveries during operation of the medical device 12. Additional neutral electrode patient ground patches (not pictured) may be employed to evaluate the desired bipolar electrical path impedance, as well as monitor and alert the operator upon detection of inappropriate and/or unsafe conditions. which include, for example, improper (either excessive or inadequate) delivery of charge, current, power, voltage and work performed by the plurality of electrodes 24; improper and/or excessive temperatures of the plurality of electrodes 24, improper electrode-tissue interface impedances; improper and/or inadvertent electrical connection to the patient prior to delivery of high voltage energy by delivering one or more low voltage test pulses to evaluate the integrity of the tissue electrical path.

The generator 14 may include an electrical current or pulse generator having a plurality of output channels, with each channel coupled to an individual electrode of the plurality of electrodes 24 or multiple electrodes of the plurality of electrodes 24 of the medical device 12. The generator 14 may be operable in one or more modes of operation, including for example: (i) bipolar energy delivery between at least two electrodes 24 or electrically-conductive portions of the medical device 12 within a patient's body, (ii) monopolar or unipolar energy delivery to one or more of the electrodes or electrically-conductive portions on the medical device 12 within a patient's body and through either a second device within the body (not shown) or a patient return or ground electrode (not shown) spaced apart from the plurality of electrodes 24 of the medical device 12, such as on a patient's skin or on an auxiliary device positioned within the patient away from the medical device 12, for example, and (iii) a combination of the monopolar and bipolar modes.

Figure 2:
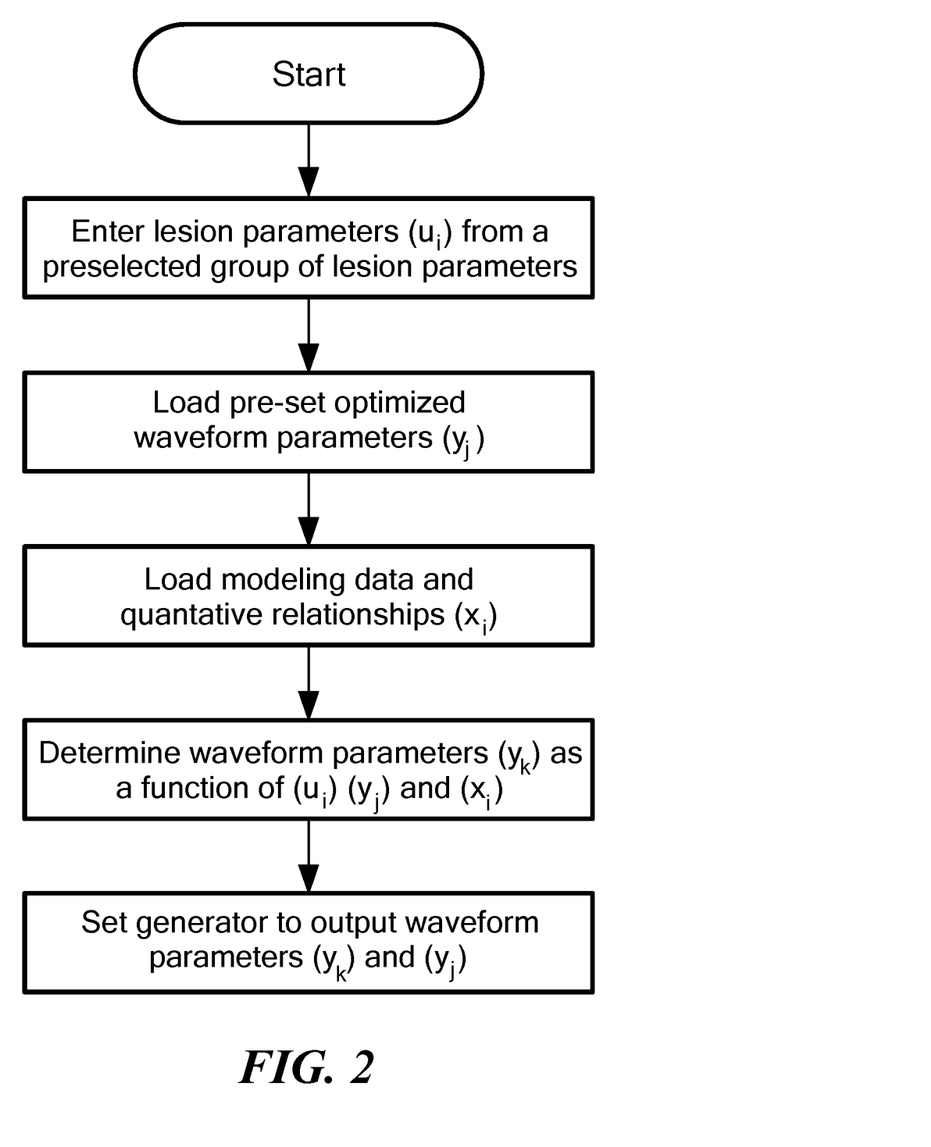
FIG. 2 is a flow chart illustrating the steps of determining a PFA waveform from a desired lesion characteristic.
Figure 3:
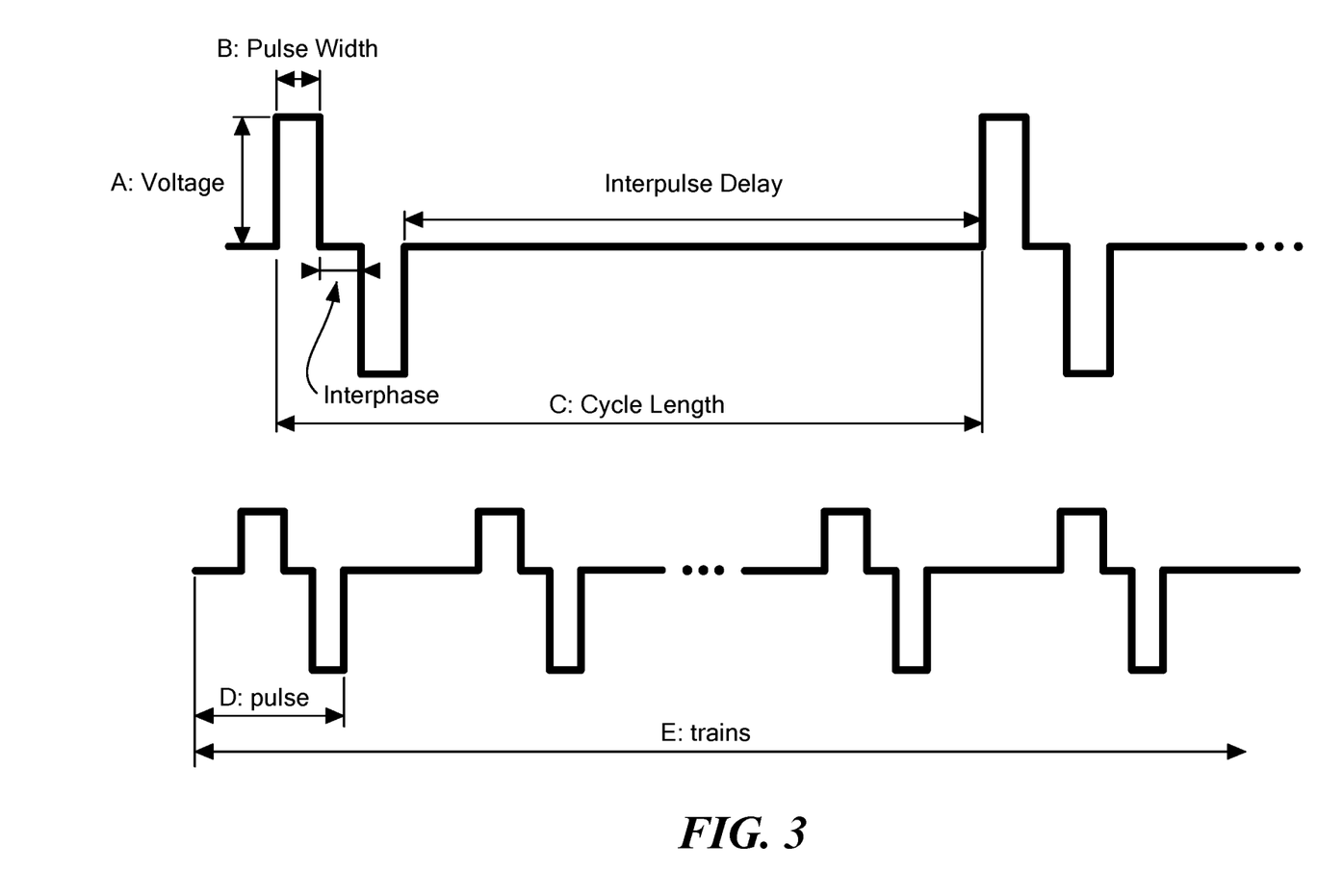
FIG. 3 shows an exemplary PFA waveform and its parameters.

Referring now to FIG. 2, a PFA waveform parameter selection algorithm may be programmed into the first processor configured to correlate a desired treatment outcome to energy settings in the generator. For example, the user may be desirous to create a lesion of a particular length, width, surface area, and/or depth for a particular tissue, but does not know the waveform parameters to create such a lesion. The exemplary algorithm described herein correlates the desired lesion characteristics to outputted waveform parameters. In one configuration, modeled lesion characteristics ($x_i$) are a function of the delivered waveform parameters ($y_i$) and user inputs ($u_i$). The delivered waveform parameters ($y_i$) may include, but are not limited to, the number of pulses, duration of each pulse, number of pulse trains, applied voltage, electrode polarity configuration, inter-pulse timing and the timing of the cycle length. Exemplary parameters of the delivered waveform are shown in FIG. 3. The user inputs ($u_i$) may include, but are not limited to, the type of catheter being used, i.e. the particular arrangement, inter-electrode spacing, and number of electrodes 26 at the distal portion of the medical device 12, which may be linear, spiral shaped, circular, or other electrodes 26 arrangements, which is a function of a particular medical device 12; the type of target tissue, for example, cardiac tissue, vascular tissue, cancerous tissue, or other types of tissue; the desired lesion characteristics, for example, depth, for example 1-10 mm, the desired lesion surface are, the desire lesion length, the design lesion width, and the desired inter-electrode lesion depth.

Through experimental modeling, the following are examples of calculations to determine various lesion characteristics ($x_i$) in myocardial tissue which function as the modeling data and parameters for the medical device 12, most exemplary for medical device 20 with distal portion 20 having a plurality of electrodes of a diameter of 1-2 mm, a length of 3-4 mm, and an inter-electrode spacing of 3-5 mm whereas the energy is passing between the positive and negative electrodes as designated in FIG. 1:

Average($x_i$)Depth=0.276+0.001943 Voltage−0.0650 Pulse Width+0.01874 Pulses+0.0980 Trains+ 0.00186 Pulse Width*Pulse Width−0.000070 Pulses*Pulses.

Average($x_i$)Surface Width=−0.65+0.00617 Voltage+ 0.1454 Pulse Width+0.03167 Pulses+0.1881 Trains−0.000124 Pulses*Pulses−0.000192 Voltage*Pulse Width.

Average($x_i$)Depth(inter-electrode)=−6.40+0.01135 Voltage+0.1471 Pulse Width+0.02005 Pulses+ 0.329 Trains−0.000005 Voltage*Voltage− 0.000104 Pulses*Pulses−0.01612 Trains*Trains−0.000116 Voltage*Pulse Width− 0.00957 Pulse Width*Trains+0.001306 Pulses*Trains.

Experimental modeling indicates certain of the waveform parameters (y) which are divided into variable ($y_k$) which are statistically significant ablation variables in determining modeled lesion characteristics ($x_i$) and thus are represented in the above models, and other waveform parameters are not statistically significant for a given characteristic, that may be set by other means such as safety considerations, and thus are preset as constant waveform parameters ($y_j$) to either limit the amount of energy delivered, limit bubble production from the electrodes, limit to time of delivery, limit embolic loads, reduce unintended muscle stimulation, or a combination of each. In one embodiment, inter-pulse timing and inter-phase timing are parameters that are set as constants and cannot be modified by the user. Other parameters, for example, pulse width are set at values to minimize bubble formation at the electrodes 24. In particular, when the pulse width is set at between 1-6 μs and in an exemplary configuration 5 μs, bubble formation is minimized while maximizing lesion formation. Moreover, the number of pulses may also be set as a constant to achieve a maximized lesion depth as adding additional pulses may not reduce the existing tissue damage, but does contribute to unnecessary bubble, energy, time, and/or coagulation delivery. Thus, the number of pulses is set to provide the most efficacious use of the energy given other potential concerns. For example, the number of pulses may be set as a constant at between 30-140 pulses (120 pulses in an exemplary configuration) and may not be modified by the user. Thus, voltage and/or electric field and the number of pulse trains delivered are the remaining parameters that the model determines and optimizes as a function of the user inputs ($u_i$). The voltage and the number of pulse trains delivered are identified as waveform parameters ($y_k$) which may be optimized and determined based on the model. Moreover, the number of applications is also a factor that has been identified as contributing to lesion depth.

In an exemplary configuration based on the parameters discussed above, for a single train delivery to achieve a given lesion depth, the following equation applies: Depth=f (Voltage)+C=A*Voltage+C±model error, where C is a function of ($y_k$) and ($y_i$) and depth is ($u_i$). So in specifying the desired depth ($u_i$), the model may set (for example) the voltage level of the delivery from reversing the determined relationship to, for example: Voltage delivered=(DepthDesired−C (+model error))/A; or stated more generally:

$$(y_k)=f((y_i),(u_i), \text{ and } (x_i))$$

The voltage level may be subject to a minimum and maximum achievable level as set by the generator 14 for, for example, safety precautions. So if the above relationship does not have a satisfactory solution (i.e. required depth is too large for the maximum allowable voltage), it could additionally specify the required number of deliveries (number of pulsed trains) to ensure the value is achieved or alert the user to unacceptable inputs. However, the model may assume a constant four pulse trains, with acceptable embolic loads, across a range of depths that correspond to different profiles, safety concerns, and a nominal dosing set. For example, the model assumes that the user would input a desired lesion depth between 1 mm and 8 mm, which correspondingly leads to the pre-set waveform parameters. The above model is also dependent on the medical device 12 and the arrangement of the plurality of electrodes 26 and is dependent on the type of tissue being treated, namely, cardiac tissue.

Figure 4:
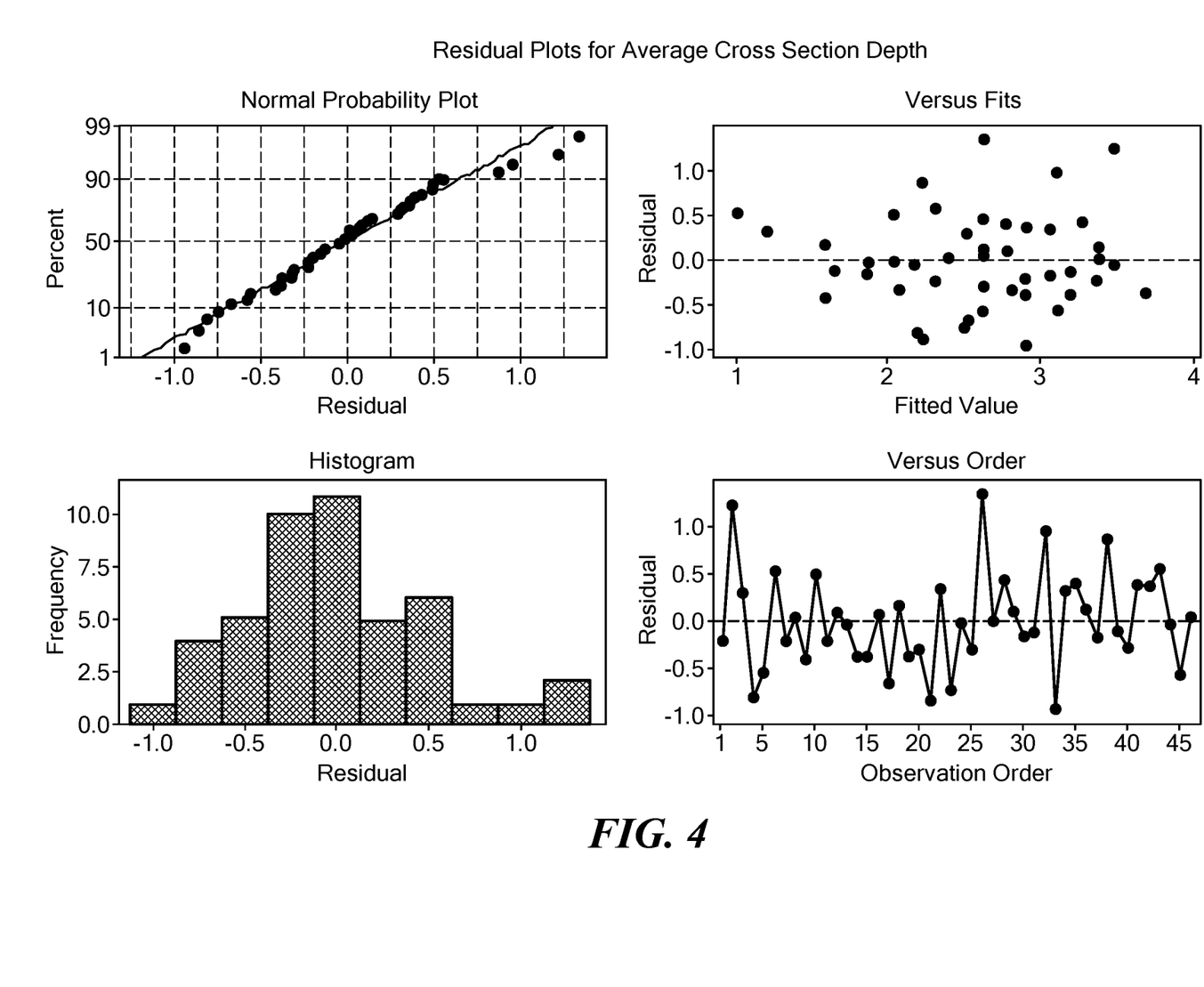
FIG. 4 shows residual plots for average cross-section lesion depth as compared to the exemplary model's predicted results.

The above model uses electroporation to non-encompassed tissue, effectively causing the electroporated region to be that volume projecting away from the electrodes 26 instead of between those electrodes 26. This results in well-defined and repeatable lesion regions, which is distinct from encompassed tissue treated by monopolar radio frequency (RF) or traditional electroporation procedures, which would have a much larger error in lesion depth calculations. Indeed, residual plot analysis of the model, as shown in FIG. 4, illustrates that the model results are accurate and illustrates a quadratic relationship between the variables. Therefore, the model provides results that represent the measured actual data.

It will be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings without departing from the scope of the application.

What is claimed is:

1. A pulsed field ablation instrument, comprising:
   a processing circuitry configured to
      receive an input of a lesion characteristic, and
      select at least one predetermined waveform parameter from a set of predetermined waveform parameters based on a statistical significance of the selected at least one predetermined waveform parameter in determining the lesion characteristic, the statistical significance being determined from experimental modeling data that relates pulsed field ablation waveform parameters to lesion characteristics; and
   a plurality of electrodes configured to deliver a pulsed field waveform generated via an electrosurgical generator and determined based on the selected at least one predetermined waveform parameter.

2. The pulsed field ablation instrument of claim 1, wherein the processing circuitry is further configured to segregate predetermined waveform parameters of the set of predetermined waveform parameters based on the statistical significance of the at least one predetermined waveform parameter in determining the lesion characteristic.

3. The pulsed field ablation instrument of claim 2, wherein the processing circuitry is further configured to separate the set of predetermined waveform parameters into a set of statistically significant waveform parameters and a set of non-statistically significant waveform parameters based on the statistical significance of the at least one predetermined waveform parameter in determining the lesion characteristic, and
   wherein the selected at least one predetermined waveform parameter is included in the set of statistically significant waveform parameters.

4. The pulsed field ablation instrument of claim 3, wherein the processing circuitry is configured to:
   set each non-statistically significant waveform parameter of the set of non-statistically significant waveform parameters as a constant value; and
   limit the pulsed field waveform based on the set of non-statistically significant waveform parameters.

5. The pulsed field ablation instrument of claim 1, wherein the experimental modeling data includes an equation that provides a numerical value of the lesion characteristic based on a numerically determined function of the pulse field ablation waveform parameters.

6. The pulsed field ablation instrument of claim 1, wherein the selecting is further based at least in part on at least one waveform parameter threshold limiting a range of the waveform parameter corresponding to the waveform parameter threshold.

7. The pulsed field ablation instrument of claim 1, wherein the experimental modeling data is based at least in part on an arrangement of at least one of the plurality of electrodes and a type of tissue to be treated.

8. The pulsed field ablation instrument of claim 1, wherein the selected at least one predetermined waveform parameter includes at least one of a number of pulses, a duration of a pulse, a number of pulse trains, and an applied voltage.

9. The pulsed field ablation instrument of claim 1, wherein the processing circuitry is further configured to select the at least one predetermined waveform parameter based at least in part on at least one of a type of pulsed field ablation catheter to deliver the determined pulsed field waveform, a configuration of the plurality of electrodes, and a shape of an electrode of the plurality of electrodes.

10. The pulsed field ablation instrument of claim 1, wherein the lesion characteristic is chosen from a set that includes at least one of a lesion depth, lesion width, lesion surface area, and an inter-electrode lesion depth.

11. The pulsed field ablation instrument of claim 1, wherein the experimental modeling data is based at least in part on a correlation between the lesion characteristic and waveform parameters of a pulsed field waveform.

12. The pulsed field ablation instrument of claim 1, wherein the selecting is further based at least in part on at least one of a limit on energy of a pulse, a limit on time of delivery of pulses, and a limit to bubble production from the plurality of electrodes.

13. A method in a pulsed field ablation instrument, the method comprising:
receiving via a processor having a processing circuitry an input of a lesion characteristic;
selecting via the processing circuitry at least one predetermined waveform parameter from a set of predetermined waveform parameters based on a statistical significance of the selected at least one predetermined waveform parameter in determining the lesion characteristic, the statistical significance being determined from experimental modeling data that relates pulsed field ablation waveform parameters to lesion characteristics; and
delivering via an electrosurgical generator coupled to a plurality of electrodes a pulsed field waveform determined based on the selected at least one predetermined waveform parameter.

14. The method of claim 13, further comprising segregating predetermined waveform parameters of the set of predetermined waveform parameters based on the statistical significance of the at least one predetermined waveform parameter in determining the lesion characteristic.

15. The method of claim 14, further comprising:
separating the set of predetermined waveform parameters into a set of statistically significant waveform parameters and a set of non-statistically significant waveform parameters based on the statistical significance of the at least one predetermined waveform parameter in determining the lesion characteristic,
wherein the selected at least one predetermined waveform parameter is included in the set of statistically significant waveform parameters.

16. The method of claim 15, further comprising:
setting each non-statistically significant waveform parameter of the set of non-statistically significant waveform parameters as a constant value; and
limiting the pulsed field waveform based on the set of non-statistically significant waveform parameters.

17. The method of claim 13, wherein the experimental modeling data includes an equation that provides a numerical value of the lesion characteristic based on a numerically determined function of the pulse field ablation waveform parameters.

18. The method of claim 13, wherein the selecting is further based at least in part on at least one waveform parameter threshold limiting a range of the waveform parameter corresponding to the waveform parameter threshold.

19. The method of claim 13, wherein the experimental modeling data is based at least in part on an arrangement of at least one of the plurality of electrodes and a type of tissue to be treated.

20. The method of claim 13, wherein the selected at least one predetermined waveform parameter includes at least one of a number of pulses, a duration of a pulse, a number of pulse trains, and an applied voltage.

21. The method of claim 13, further comprising selecting the at least one predetermined waveform parameter based at least in part on at least one of a type of pulsed field ablation catheter to deliver the determined pulsed field waveform, a configuration of the plurality of electrodes, and a shape of an electrode of the plurality of electrodes.

22. The method of claim 13, wherein the lesion characteristic is chosen from a set that includes at least one of a lesion depth, lesion width, lesion surface area, and an inter-electrode lesion depth.

23. The method of claim 13, wherein the experimental modeling data is based at least in part on a correlation between the lesion characteristic and waveform parameters of a pulsed field waveform.

24. The method of claim 13, wherein the selecting is further based at least in part on at least one of a limit on energy of a pulse, a limit on time of delivery of pulses, and a limit to bubble production from the plurality of electrodes.

* * * * *